United States Patent
Zhou et al.

(10) Patent No.: US 10,058,817 B2
(45) Date of Patent: Aug. 28, 2018

(54) CONTINUOUS OPERABLE GAS PURIFICATION DEVICE IN AN ION MOBILITY SPECTROMETER

(71) Applicant: Nuctech Company Limited, Beijing (CN)

(72) Inventors: Haichao Zhou, Beijing (CN); Yangtian Zhang, Beijing (CN); Yuntai Bao, Beijing (CN); Wangyang Wu, Beijing (CN); Yi Xiao, Beijing (CN); Changzhuo Chen, Beijing (CN); Qifang Wang, Beijing (CN); Wen He, Beijing (CN); Haijun Yu, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 210 days.

(21) Appl. No.: 15/067,349

(22) Filed: Mar. 11, 2016

(65) Prior Publication Data
US 2016/0263520 A1   Sep. 15, 2016

(30) Foreign Application Priority Data
Mar. 12, 2015 (CN) .......................... 2015 1 0109230

(51) Int. Cl.
*B01D 53/02* (2006.01)
*B01D 53/26* (2006.01)
(Continued)

(52) U.S. Cl.
CPC ............ *B01D 53/261* (2013.01); *B01D 53/06* (2013.01); *B01D 2257/80* (2013.01); *G01N 27/622* (2013.01)

(58) Field of Classification Search
CPC .. B01D 2257/80; B01D 53/06; B01D 53/261; G01N 27/622
See application file for complete search history.

(56) References Cited

U.S. PATENT DOCUMENTS

| | | | | |
|---|---|---|---|---|
| 4,551,624 A | * | 11/1985 | Spangler | G01N 30/70 250/282 |
| 4,719,761 A | * | 1/1988 | Cromer | F24F 3/1405 62/271 |

(Continued)

FOREIGN PATENT DOCUMENTS

| | | |
|---|---|---|
| CN | 1703266 A | 11/2005 |
| CN | 101101140 A | 1/2008 |

(Continued)

OTHER PUBLICATIONS

Zhu, Kunjie et al., "Medical Functional Experiments", Peking University Medical Press, Sep. 30, 2006, pp. 114-117.
(Continued)

*Primary Examiner* — Christopher P Jones
(74) *Attorney, Agent, or Firm* — Scully, Scott, Murphy & Presser, P.C.

(57) ABSTRACT

The present disclosure discloses a continuous operable gas purification device in an ion mobility spectrometer including a housing provided with a cylinder cavity; a dry gas supply unit; a rotating barrier arranged in a radial direction of the cylinder cavity to divide it into a baking cavity and a working cavity; and a rotating mechanism. The housing is provided with a dry gas inlet and a dry gas outlet, which are communicated with the baking cavity, and a sample gas inlet and a sample gas outlet, which are communicated with the working cavity. The dry gas supply unit is connected with the dry gas inlet for a dry gas supply to the dry gas inlet. The baking cavity is provided with a heating unit correspondingly. The rotating mechanism is provided at a central position of the cylinder cavity and connected with the rotating barrier for rotating it at intervals.

11 Claims, 1 Drawing Sheet

(51) Int. Cl.
*G01N 27/62* (2006.01)
*B01D 53/06* (2006.01)

(56) References Cited

U.S. PATENT DOCUMENTS

| | | | | |
|---|---|---|---|---|
| 5,289,695 | A * | 3/1994 | Parrish | F25B 17/08 62/259.3 |
| 5,514,035 | A * | 5/1996 | Denniston | B60H 1/00414 454/121 |
| 5,873,256 | A * | 2/1999 | Denniston | B60H 1/00414 62/244 |
| 5,878,590 | A * | 3/1999 | Kadle | B60H 3/024 165/165 |
| 5,980,615 | A * | 11/1999 | Roe | B01D 53/0415 96/111 |
| 6,318,106 | B1 * | 11/2001 | Maeda | F24F 3/1423 62/238.3 |
| 2008/0191132 | A1 * | 8/2008 | Boyle | G01N 27/624 250/287 |
| 2009/0229461 | A1 | 9/2009 | Jeng et al. | |
| 2010/0281905 | A1 * | 11/2010 | Takatsuka | B01D 53/08 62/271 |
| 2011/0083458 | A1 * | 4/2011 | Takakura | B01D 53/0454 62/176.1 |
| 2011/0303024 | A1 * | 12/2011 | Wallis | G01N 1/2247 73/863.21 |
| 2012/0037002 | A1 * | 2/2012 | Frydman | B01D 53/06 96/118 |
| 2012/0068061 | A1 * | 3/2012 | Griffin | G01N 1/24 250/282 |
| 2012/0204718 | A1 * | 8/2012 | Dinnage | B01D 53/06 95/91 |
| 2013/0112079 | A1 * | 5/2013 | Shih | B01D 53/261 96/54 |
| 2013/0234013 | A1 * | 9/2013 | Patterson | G01N 1/2205 250/282 |
| 2013/0269522 | A1 * | 10/2013 | DeValve | F24F 3/1411 95/91 |
| 2015/0362228 | A1 * | 12/2015 | Ivashin | F25B 21/02 62/601 |
| 2016/0349211 | A1 | 12/2016 | Bao et al. | |

FOREIGN PATENT DOCUMENTS

| | | | |
|---|---|---|---|
| CN | 102226552 | A | 10/2011 |
| CN | 102481511 | A | 5/2012 |
| CN | 102586524 | A | 7/2012 |
| CN | 202734465 | U | 2/2013 |
| CN | 103237589 | A | 8/2013 |
| CN | 203899420 | U | 10/2014 |
| CN | 104201083 | A | 12/2014 |
| CN | 104759189 | A | 7/2015 |
| CN | 204485605 | U | 7/2015 |
| DE | 10 2008 023 791 | A | 12/2009 |
| DE | 20 2014 007 507 | U1 | 12/2014 |
| JP | S56-154824 | A | 11/1981 |
| JP | H11-268527 | A | 10/1999 |
| JP | 2003-533339 | A | 11/2003 |

OTHER PUBLICATIONS

International Search Report dated Mar. 15, 2016 received in PCT/CN2015/096850.

* cited by examiner

CONTINUOUS OPERABLE GAS PURIFICATION DEVICE IN AN ION MOBILITY SPECTROMETER

CROSS-REFERENCE TO RELATED APPLICATIONS

This application is based upon and claims priority to Chinese Patent Application No. 201510109230.6, filed on Mar. 12, 2015, which is incorporated herein by reference in its entirety.

TECHNICAL FIELD

The disclosure relates to the detection field, and more particularly, to a continuous operable gas purification device in an ion mobility spectrometer.

BACKGROUND

In order to keep the gases entering into a trace detecting device, such as an ion mobility spectrometer clean, the gases entering into the ion mobility spectrometer is generally purified by using a gas purification device. The moisture and impurity in the gas are removed mainly by the desiccant in the gas purification device during a gas purifying process, and the desiccant is renewable by a series of high temperature baking and cooling processes so as to be recycled.

In the existing ion mobility spectrometers, a single gas purification device is used in some ion mobility spectrometers, in which the gas is dried by the desiccant disposed in the gas purification device, which requires replaced periodically in a short time. During the replacement, the ion mobility spectrometer cannot be used nor continuous work, and thus the maintenance cost is high. Moreover, two gas purification devices are used in some ion mobility spectrometers, in which the gas is dried in turn by the desiccants disposed in the gas purification devices, that is, when replacing one gas purification device, the other one is used, so as to achieve continuous works. However, in this case, the gas purification device is required to be replaced periodically and the desiccant is not recyclable. Therefore, the gas purification devices in the existing ion mobility spectrometers have disadvantages of manual replacement, low efficiency and high cost.

SUMMARY

The object of the present disclosure is to provide a continuous operable gas purification device in an ion mobility spectrometer, such that the gas purification device is not required to be replaced manually during the detecting process, and a high efficiency and a low labor cost are caused.

In order to solve above technical problem, the present disclosure provides a continuous operable gas purification device in an ion mobility spectrometer including: a housing provided with a cylinder cavity; a dry gas supply unit; a rotating barrier arranged in a radial direction of the cylinder cavity to divide it into a baking cavity and a working cavity; and a rotating mechanism. The housing may be provided with a dry gas inlet, a dry gas outlet, a sample gas inlet and a sample gas outlet. The dry gas inlet and the dry gas outlet may both be communicated with the baking cavity, while the sample gas inlet and the sample gas outlet may both be communicated with the working cavity. The dry gas supply unit may be connected with the dry gas inlet for a dry gas supply to the dry gas inlet. The baking cavity may be provided with a heating unit correspondingly. The rotating mechanism may be provided at the central position of the cylinder cavity and connected with the rotating barrier for rotating the rotating barrier at intervals.

Wherein, a sealing strip may be provided between the rotating barrier and a wall surface of the cylinder cavity.

Wherein, the housing may include a bottom case in which the cylinder cavity may be formed and an upper cover connected with the bottom case through a sealing element in an air-tight manner.

Wherein, the gas purification device may further include two desiccant boxes for containing the desiccants, which may be provided in the baking cavity and the working cavity respectively.

Wherein, a plurality of guide baffles may be provided in the desiccant box.

Wherein, the rotating mechanism may include a rotating shaft mounted at the center of the cylinder cavity and fixed with the rotating barrier, and a rotating motor dynamically connected with the rotating shaft.

Wherein, the rotating motor may be a direct drive motor.

Wherein, the dry gas inlet and the sample gas inlet may be arranged in a central symmetry way about the axis center of the rotating shaft.

Wherein, the gas purification device may further include a rotating controller connected with the rotating mechanism for sending a control command to the rotating mechanism as required so as to control the rotating mechanism to drive the rotating barrier rotating 180 degrees.

Wherein, the gas purification device may further include a heating controller connected with the heating unit, for controlling a temperature and a heating time of the baking cavity.

In the continuous operable gas purification device in the ion mobility spectrometer provided by the present disclosure, the cylinder cavity divided into the baking cavity and the working cavity by the rotating barrier is provided in the housing, and the desiccant is circularly moved in the baking cavity and the working cavity by the rotating barrier to obtain a continuous gas purifying during the detecting process without manual replacement of the desiccant, thereby the work efficiency is improved; the desiccant is recycled such that the amount of the desiccant and the detection cost are reduced.

Figure 1:
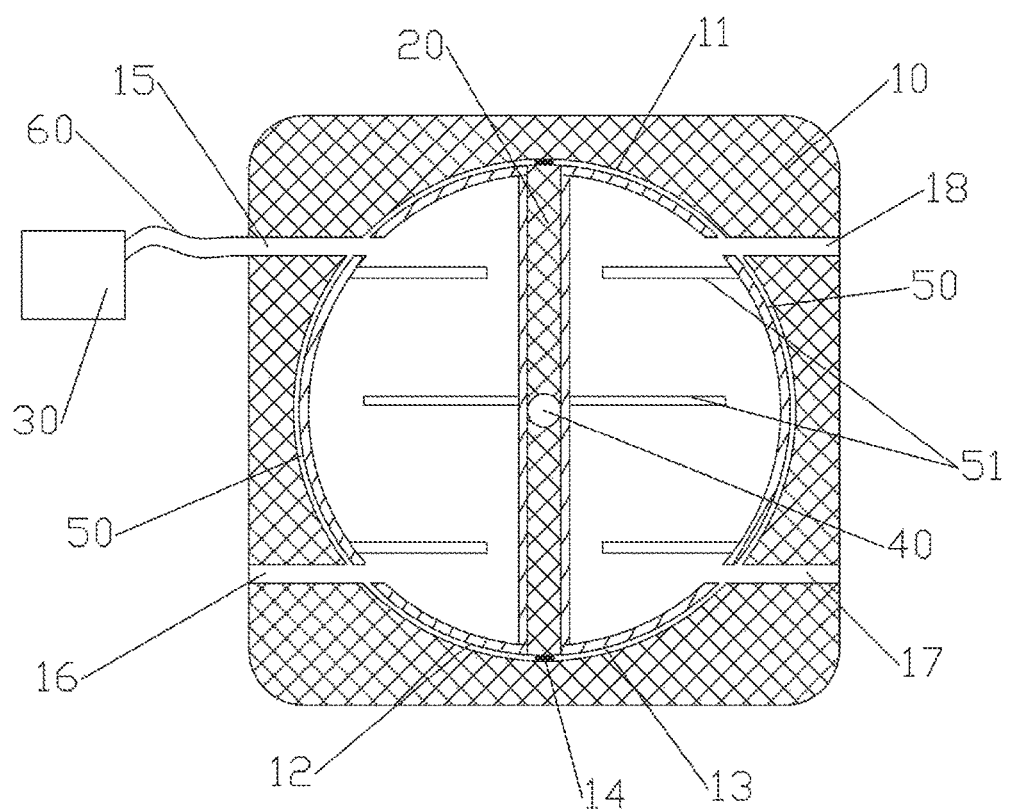
FIG. 1 is a cross-sectional view of an embodiment of the present disclosure.

In the drawings, reference numbers with the corresponding features are as follows:

10: housing; 11: cyclinder cavity; 12: baking cavity; 13: working cavity; 14: sealing strip; 15: dry gas inlet; 16: dry gas outlet; 17: sample gas inlet; 18: sample gas outlet; 20: rotating barrier; 30: dry gas supply unit; 40: rotating mechanism; 41: rotating motor; 42: rotating shaft; 50: desiccant box; 51: guide baffle; 60: conduit; 70: heating unit; 101: bottom case; 102: cover plate.

DETAILED DESCRIPTION

Detailed description of the present disclosure will be further made below in combination with drawings and embodiments. The following examples are used to explain the present disclosure, rather than to limit the scope of the present disclosure.

Figure 2:
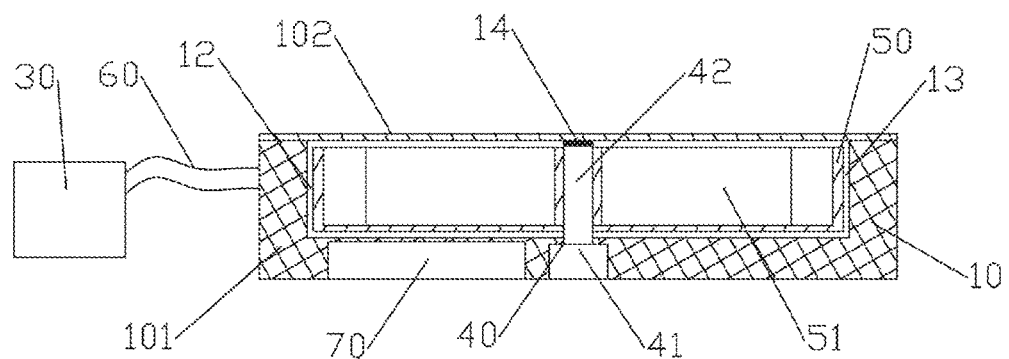
FIG. 2 is a longitudinal sectional view of the embodiment of the present disclosure.

With reference to FIGS. 1 and 2, a continuous operable gas purification device in an ion mobility spectrometer of the present disclosure includes: a housing 10 provided with a cylinder cavity 11; a dry gas supply unit 30; a rotating barrier 20 arranged in a radial direction of the cylinder cavity 11 to divide it into a baking cavity 12 and a working cavity 13; and a rotating mechanism 40. The housing 10 is provided with a dry gas inlet 15, a dry gas outlet 16, a sample gas inlet 17 and a sample gas outlet 18. Both the dry gas inlet 15 and the dry gas outlet 16 are communicated with the baking cavity 12, and both the sample gas inlet 17 and the sample gas outlet 18 are communicated with the working cavity 13. The dry gas supply unit 30 is connected with the dry gas inlet 15 through a conduit 60 for a dry gas supply to the dry gas inlet 15. The baking cavity 12 is provided with a heating unit 70 correspondingly, which is provided under the baking cavity 12 in this embodiment. The rotating mechanism 40 is provided at the central position of the cylinder cavity 11 and is connected with the rotating barrier 20 for rotating the rotating barrier 20 at intervals. The rotating barrier rotates 180 degrees every time.

In use, the sample gas inlet 17 is connected with a sample gas supply unit, while the sample gas outlet 18 is connected with a detecting unit of the ion mobility spectrometer. After filling the baking cavity 12 and the working cavity 13 with the desiccants, the sample gas is introduced from the sample gas inlet 17, dried by the desiccant and discharged from the sample gas outlet 18, such that a purification of the sample gas is completed. After being used for a period time (2 hours in this embodiment), the desiccant in the working cavity 13 absorbs moisture and impurity and fails to dry the sample gas any more. At this moment, the rotating mechanism 40 drives the rotating barrier rotating 180 degrees so that the desiccants in the working cavity 13 are moved into the baking cavity 12 and the desiccants in the baking cavity 12 are moved into the working cavity 13 to enable the working cavity 13 to purify the sample gas continuously; simultaneously, the heating unit 70 and the dry gas supply unit 30 are started, so that the baking cavity 12 is heated by the heating unit 70 to keep the desiccant therein at a temperature of 100-200° C. In this way, the moisture in the desiccant is evaporated and the impurity in the desiccant is gasified. The dry gas (the dried air in this embodiment) is introduced to the baking cavity 12 through the dry gas inlet 15 by the dry gas supply unit 30, while the dry gas flows through the desiccant, the evaporated moisture and impurity are removed and then discharged from the dry gas outlet 16. After the heating unit 70 operating for 50-70 minutes, such as 50 minutes, 60 minutes or 70 minutes, the heating unit 70 is stopped, while the dry gas is successively supplied by the dry gas supply unit 30 to cool the desiccant to an indoor temperature. After 2 hours interval, the desiccant in the working cavity 13 is invalided. At this moment, the rotating barrier 20 is successively rotated to exchange the desiccants in the baking cavity 12 and the working cavity 13 in order to enable the gas purification device to work continuously. The above processes are repeated such that a continuous gas purifying is achieved without manual replacement of the desiccants, thereby improves the working efficiency. The rotating barrier drives the desiccant to be rotated together such that the desiccant is reciprocated between the working cavity and the baking cavity and used repeatedly. As a result, the amount of the desiccant to be used is reduced, and the detection cost is also low.

Further, a sealing strip 14 is provided between the rotating barrier 20 and a wall surface of the cylinder cavity 11. The sealing strip 14 is made from polytetrafluoroethylene material or silica gel material, or other sealing materials with high temperature resistance and aging resistance. The sealing strip is used to facilitate the isolation between the baking cavity 12 and the working cavity 13, thereby improve the precision of gas purifying.

Further, the housing 10 includes a bottom case 101 in which the cylinder cavity 11 is formed and an upper cover 102 connected with the bottom case 101 through a sealing element in an air-tight manner. Referring to FIGS. 1 and 2, the sealing strips are provided between an upper surface of the rotating barrier 20 and the upper cover, and between the rotating barrier 20 and an inside wall surface of the cylinder cavity 11.

Further, the gas purification device further includes two desiccant boxes 50 for containing desiccant, which are provided in the baking cavity 12 and the working cavity 13 respectively. The appearance of the desiccant box 50 is a semi-cylinder which matches the shape of the working cavity 13 and the baking cavity 12, and may be made with a closed structure or a mesh structure. Mesh holes corresponding to the sample gas inlet 17 and the sample gas outlet 18 (or the dry gas inlet 15 and the dry gas outlet 16) are provided on the side wall of the desiccant boxes 50 with a closed structure. When the desiccants are contaminated and completely unable to recover after used for a long time, it only requires to replace the desiccants by withdrawing the desiccant box 50. Therefore, replacement of the desiccant is improved.

Further, a plurality of guide baffles 51 are provided in the desiccant box 50. Gas (the sample gas or the dry gas) flows sinuously in the desiccant boxes 50 by providing the guide baffles 51 in the desiccant box 50, thereby increases the contact area between desiccant and gas and enhances the purifying and baking effect.

Further, the rotating mechanism 40 includes a rotating shaft 42 mounted at the center of the cylinder cavity 11 and fixedly connected with the rotating barrier 20, and a rotating motor 41 dynamically connected with the rotating shaft 42. Preferably, the rotating motor 41 is a direct drive motor. The dry gas inlet 15 and the sample gas inlet 17 are arranged in a central symmetry way about the axis center of the rotating shaft 42. The rotating mechanism 40 is not limited to the structure of this embodiment; it can also be implemented by those skilled in the art with other implementation methods, which will not be described in detail.

Further, the gas purification device further includes a rotating controller and a heating controller (not shown in the drawings). The rotating controller is connected with the rotating mechanism 40 for sending a control command to the rotating mechanism 40 as required to control the rotating mechanism 40 to drive the rotating barrier 20 rotating 180 degrees. It should be noted that, the rotating barrier 20 of the present disclosure may rotate 180 degrees in the same direction every time, and may also rotate in opposite directions every adjacent two times, i.e., it rotates 180 degrees clockwise at one time and then rotates 180 degrees counterclockwise next time. The heating controller is connected with the heating unit 70 for controlling the temperature and heating time of the baking cavity 12. The heating controller includes sensor and calculating module connected each other. The sensor is mounted in the baking cavity 12 to detect the temperature in the baking cavity 12. When the detected temperature is above 200° C., the calculating module sends a control signal to the heating unit 70 to stop the heating unit; when the detected temperature is below 100° C., the calculating module sends a control signal to the heating unit 70 to start the heating unit. The heating controller also controls the heating time of the heating unit 70, which may be set on the heating controller as desired.

It should be noted that, the heating unit 70 may be provided under the baking cavity 12 as in this embodiment, and may also be provided above the baking cavity 12 or at a lateral position of the baking cavity 12.

Finally, it should be noted that the embodiments disclosed above should be considered as illustrative embodiments only and not intended to limit. Any modifications, equivalent substitutions and improvements should be included in the protection scope of the present disclosure without departing from the spirit and principle of the present disclosure.

What is claimed is:

1. A continuous operable gas purification device in an ion mobility spectrometer, comprising:
   a housing provided with a cylinder cavity;
   a dry gas supply unit;
   a rotating barrier arranged in a radial direction of the cylinder cavity to divide the cylinder cavity into a baking cavity and a working cavity; and
   a rotating mechanism,
   wherein the housing is provided with a dry gas inlet, a dry gas outlet, a sample gas inlet and a sample gas outlet, both the dry gas inlet and the dry gas outlet are communicated with the baking cavity, while both the sample gas inlet and the sample gas outlet are communicated with the working cavity,
   wherein the dry gas supply unit is connected with the dry gas inlet for a dry gas supply to the dry gas inlet,
   wherein the baking cavity is provided with a heating unit correspondingly, and the rotating mechanism is provided at a central position of the cylinder cavity and is connected with the rotating barrier for rotating the rotating barrier with respect to the cylinder cavity, at intervals,
   wherein the continuous operable gas purification device further comprises a desiccant box, the desiccant box has a semi-cylindrical shape and a closed structure, and mesh holes corresponding to the sample gas inlet and the sample gas outlet are provided on a side wall of the desiccant box.

2. The continuous operable gas purification device in an ion mobility spectrometer according to claim 1, wherein a sealing strip is provided between the rotating barrier and a wall surface of the cylinder cavity.

3. The continuous operable gas purification device in an ion mobility spectrometer according to claim 1, wherein the housing comprises a bottom case in which the cylinder cavity is formed and an upper cover connected with the bottom case through a sealing element in an air-tight manner.

4. The continuous operable gas purification device in an ion mobility spectrometer according to claim 1, wherein the gas purification device comprises two desiccant boxes including the desiccant box for containing desiccants, which are provided in the baking cavity and the working cavity respectively.

5. The continuous operable gas purification device in an ion mobility spectrometer according to claim 4, wherein a plurality of guide baffles are provided in each desiccant box.

6. The continuous operable gas purification device in an ion mobility spectrometer according to claim 1, wherein the rotating mechanism comprises a rotating shaft mounted at the center of the cylinder cavity and fixed with the rotating barrier, and a rotating motor dynamically connected with the rotating shaft.

7. The continuous operable gas purification device in an ion mobility spectrometer according to claim 6, wherein the rotating motor is a direct drive motor.

8. The continuous operable gas purification device in an ion mobility spectrometer according to claim 6, wherein the dry gas inlet and the sample gas inlet are arranged in a central symmetry way about an axis center of the rotating shaft.

9. The continuous operable gas purification device in an ion mobility spectrometer according to claim 1, wherein the gas purification device further comprises a rotating controller connected with the rotating mechanism for sending a control command to the rotating mechanism as desired so as to control the rotating mechanism to drive the rotating barrier rotating 180 degrees.

10. The continuous operable gas purification device in an ion mobility spectrometer according to claim 9, wherein the gas purification device further comprises a heating controller connected with the heating unit, for controlling a temperature and a heating time of the baking cavity.

11. The continuous operable gas purification device in an ion mobility spectrometer according to claim 1, wherein the cylinder cavity is stationary while the rotating barrier rotates.

* * * * *